United States Patent [19]

Hudec

[11] Patent Number: 4,982,006

[45] Date of Patent: Jan. 1, 1991

[54] PROCESS FOR THE PREPARATION OF CERTAIN SUBSTITUTED AROMATIC COMPOUNDS

[75] Inventor: Thomas T. Hudec, Norwich, N.Y.

[73] Assignee: Norwich Eaton Pharmaceuticals, Inc., Norwich, N.Y.

[21] Appl. No.: 346,427

[22] Filed: May 1, 1989

Related U.S. Application Data

[63] Continuation-in-part of Ser. No. 134,655, Dec. 18, 1987, abandoned.

[51] Int. Cl.$^5$ ............................................. C07C 45/46
[52] U.S. Cl. ..................... 568/322; 568/42; 568/43; 568/323; 544/335; 548/300; 549/39; 549/370; 549/375; 549/454; 549/462; 556/432; 556/436; 560/51; 560/53; 560/130; 564/169; 564/215; 564/288; 564/343
[58] Field of Search ............... 568/322, 323, 42, 43; 548/300; 549/39, 370, 375, 448, 454, 462; 544/335; 556/432, 436; 560/51, 53, 130; 564/169, 215, 343, 288

[56] References Cited

U.S. PATENT DOCUMENTS

| | | | |
|---|---|---|---|
| 3,717,611 | 2/1973 | Baumer et al. | 260/45.95 G |
| 3,862,133 | 1/1975 | Layer | 260/343.3 |
| 4,130,666 | 12/1978 | Moore | 424/331 |
| 4,325,863 | 4/1982 | Hinsken et al. | 624/111 |
| 4,431,656 | 2/1984 | Katsumi et al. | 424/273 R |
| 4,440,784 | 4/1984 | Katsumi et al. | 424/308 |
| 4,708,966 | 11/1987 | Loomans et al. | 568/337 |
| 4,711,903 | 12/1987 | Mueller et al. | 514/381 |
| 4,847,303 | 7/1989 | Loomans et al. | 514/689 |
| 4,849,428 | 7/1989 | Dobson et al. | 549/307 |

FOREIGN PATENT DOCUMENTS

| | | |
|---|---|---|
| 54-44627 | 9/1977 | Japan . |
| 60-54315 | 3/1985 | Japan . |
| 61-218571 | 4/1985 | Japan . |

OTHER PUBLICATIONS

Gould, Mechanism & Structure in Org. Chem., Holt, Rinehart & Winston, N.Y. (1959), pp. 220-221.
Fieser and Fieser, Reagents for Org. Synthesis, Wiley, N.Y. (1967), p. 1111.
Olah, Friedel-Crafts & Related Reactions, vol. III, Part 1, Interscience, N.Y. (1964), p. 9.
Mustafa, Benzofurans, Interscience, N.Y. (1974), pp. 188-189.
Hauff, Krauss & Rieker, "Spin Density Distribution in Free Radicals, VII, Participation of the Carbon-Carbon Bond in the Mesomerism of Phenoxy Radicals", *Chem. Ber.*, vol. 105, No. 4 (1972), pp. 1446-1455.
Gavrilov, Meshcheryakov, Kalyagina, Dobronravova & Vereshchagin, "Synthesis of Diarylpropynones and their Antibiotic Activity", *Khimiko-Farmatsevticheskii Zhurnal*, vol. 12, No. 9 (Sep. 1978), pp. 42-56.
Swingle, Bell & Moore, "Anti-Inflammatory Activity of Antioxidants", Chapter 4 of Anti-Inflammatory and Anti-Rheumatic Drugs, vol. III, Rainsford (ed.), CRC Press, Inc., Boca Raton, Fla., 1985, pp. 105-126.
*Soviet Inventions Illustrated*, Week 8429, SU 1054-34-2-A, Derwent Publications, Ltd., London, England (1984).
Magnusson, "Reactions between Quinones and Carbonyl Compounds Catalysed by Aluminum Oxide", *Acta Chemica Scandinavica*, vol. 18, No. 2 (1964), pp. 421-432.
Layer, "Synthesis of 2(3H)Benzofuranones from Glyoxal and Phenols", *Journal of Heterocyclic Chemistry*, vol. 12, No. 5 (1975), pp. 1067-1068.

*Primary Examiner*—Mary C. Lee
*Assistant Examiner*—Bernard I. Dentz
*Attorney, Agent, or Firm*—Milton B. Graff, IV; David L. Suter; Jack D. Schaeffer

[57] ABSTRACT

The present invention involves process for the preparation of compounds having the chemical structure:

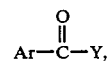

wherein Ar—H is an aromatic compound which is activated to an electrophilic attack, and wherein —Y is an aliphatic group having a labile moiety, especially where the labile moiety is a terminally unsaturated moiety: —C≡CH,

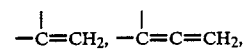

or aldehydes in the form of their acetals. The process comprises the step of reacting Ar—H and

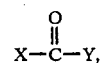

wherein —X is —Cl or —Br, and where the reaction step is carried out in a solvent medium at a temperature of from about −40° C. to about −100° C. using stannic chloride as a catalyst.

16 Claims, No Drawings

PROCESS FOR THE PREPARATION OF CERTAIN SUBSTITUTED AROMATIC COMPOUNDS

This is a continuation-in-part of application Ser. No. 134,655, filed on Dec. 18, 1987.

TECHNICAL FIELD

The present invention relates to a process for preparing certain substituted aromatic compounds, with an aliphatic ketone substituent having a labile moiety, using a modified Friedel-Crafts reaction.

BACKGROUND OF THE INVENTION

Compounds useful as anti-inflammatory agents which are aromatic compounds, especially substituted tert-butylphenol compounds, and related derivatives thereof, with an aliphatic ketone substituent having a terminally unsaturated moiety are disclosed in U.S. Pat. No. 4,708,966, issued to Loomans, Matthews & Miller on Nov. 24, 1987; and in copending patent applications entitled "Cyclic Anti-Inflammatory Derivatives of Di-tert-butylphenol Compounds" of Dobson, Loomans, Matthews & Miller, Ser. No. 123,756, and "Tert-Butyl Phenyl Compounds Useful as Anti-Inflammatory Agents of Loomans, Matthews & Miller, Ser. No. 123,694, both filed on Nov. 23, 1987.

Friedel-Crafts reactions of aromatic hydrocarbons with acyl halides in the presence of a catalyst such as anhydrous aluminum chloride to produce aromatic compounds having an aliphatic ketone substituent are well-known. However, when the acyl halide reactant has a labile portion, such as a terminally unsaturated moiety, many unwanted side reactions can occur, such that the yield of the desired product is low. This has made preparation of certain substituted aromatic compounds, with an aliphatic ketone substituent having a labile moiety, in large quantities and with good yields a difficult task.

It is an object of the present invention to provide a process for the preparation of aromatic compounds, with an aliphatic ketone substituent having a labile portion.

It is a further object of the present invention to provide a process for the preparation of such compounds from aromatic and acyl halide reactants with good yield.

SUMMARY OF THE INVENTION

The present invention relates to processes for the preparation of compounds having the chemical structure:

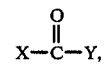

wherein Ar—H is an aromatic compound which is activated to an electrophilic attack, and wherein —Y is an aliphatic group having a labile moiety, especially where the labile moiety is a terminally unsaturated moiety: —C≡CH,

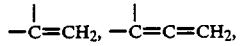

or aldehydes in the form of their acetals. The process comprises the step of reacting Ar—H and

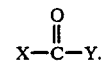

wherein —X is —Cl or —Br, and where the reaction step is carried out in a solvent medium at a temperature of from about −40° C. to about −100° C. using stannic chloride as a catalyst.

DETAILED DESCRIPTION OF THE INVENTION

The processes of the present invention comprise modified Friedel-Crafts reactions between the reactants Ar—H and

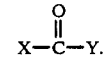

As used herein, Ar—H is an aromatic compound which is activated to electrophilic attack. Such compounds include unsubstituted and substituted phenols, anisole, 1,2-diethoxybenzene, furans, naphthols, and other substituted and unsubstituted heteroaromatics. Preferred compounds Ar—H useful in the processes of the present invention are substituted tert-butylphenol compounds, especially di-tert-butylphenol compounds and derivatives thereof.

Preferred compounds Ar—H useful in the processes of the present invention have the general structure:

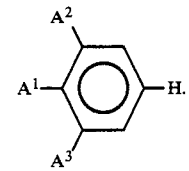

In this structure, —$A^1$ is selected from the group consisting of —OH, —H, —$O_2$CR, wherein —R is a straight or branched chain alkyl group having from 1 to about 10 carbon atoms, preferably methyl or ethyl. Preferred —$A^1$ is —OH or —H, and most preferred —$A^1$ is —OH.

—$A^2$ is selected from the group consisting of unsubstituted or substituted, saturated or unsaturated, straight, branched or cyclic alkyl having from 1 to about 10 carbon atoms and trimethylsilyl. Substituents of —$A^2$ may be one or more of the group consisting of halo, —$OR^3$, —$O_2CR^3$, —$CO_2R^3$, and —$C(O)R^3$. Preferred is unsubstituted —$A^2$ or —$A^2$ substituted with hydroxy or halo, especially fluoro. More preferred —$A^2$ is selected from unsubstituted $C_1$-$C_3$ saturated straight-chain alkyl, $C_2$-$C_6$ unsaturated straight-chain alkyl, and $C_3$-$C_6$ saturated or unsaturated branched-chain alkyl, trimethylsilyl and trifluoromethyl. Preferred unsaturated —$A^2$'s have a terminally unsaturated group; where —$A^2$ has a labile moiety, a blocking group may be attached to the labile group prior to reacting Ar—H with Most preferred $A^2$ is t-butyl.

—$A^3$ is selected from the group consisting of t-butyl, trimethylsilyl and trifluoromethyl. Preferably —$A^2$ and —$A^3$ are the same substituent. Preferred —$A^3$ is t-butyl.

Preferred compounds Ar—H useful in the processes of the present invention also include derivatives of tert-butylphenol compounds, especially derivatives of di-tert-butylphenol compounds; particularly preferred are those having the structure:

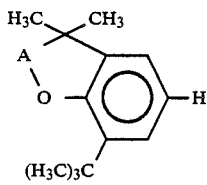

In this structure, —A— is selected from the group consisting of —$CH_2$—,

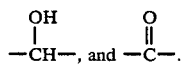

Preferred —A— is —$CH_2$— or

and most preferred —A— is —$CH_2$—.

As used herein, compounds

are acyl chloride or bromide compounds (—X═—Cl or —Br, preferably —Cl), wherein —Y is a terminally unsaturated group selected from the group consisting of:

1. —$(CR^1{}_2)_n$—C≡CH, wherein n is an integer from 0 to about 5;
2. —$(CR^1{}_2)_n$—$CR^3$═$CH_2$, wherein n is an integer from 0 to about 5;
3. —$(CR^1{}_2)_n$—$CR^3$═C═$CH_2$, wherein n is an integer from 0 to about 5; and
4. —$(CR^1{}_2)_n$—$CH(ZR^4)_2$, wherein n is an integer from 1 to about 5;

and wherein each —$R^1$ is independently selected from the group consisting of —H, —$OR^3$, —$NR^3{}_2$, —$NR^3{}_3{}^+$, —$N(R^3)C(O)R^3$, —$O_2CR^3$, —$CO_2R^3$, —$C(O)NR^3{}_2$, straight or branched chain saturated alkyl group having from 1 to about 3 carbon atoms, and straight or branched chain unsaturated alkyl group having from 2 to about 3 carbon atoms, or two —$R^1$'s on the same carbon atom are ═O or ═$CR^3{}_2$; each —$R^3$ is independently selected from the group consisting of —H, methyl and ethyl; each —$R^4$ is independently selected from the group consisting of —$CH_3$ and —$CH_2CH_3$, or the —$R^4$'s may be joined to form a cyclic acetal such that both —$R^4$'s together are one group selected from —$(CH_2)_2$— and —$(CH_2)_3$—; and each —Z— is independently selected from the group consisting of —O—, —S—, and —$NR^3$—.

In these substituent —Y groups, each —$R^1$ is independently selected from the group consisting of —H, —$OR^3$, —$NR^3{}_2$, —$NR^3{}_3{}^+$, —$N(R^3)C(O)R^3$, —$O_2CR^3$, —$CO_2R^3$, —$C(O)NR^3{}_2$, straight or branched chain saturated alkyl group having from 1 to about 3 carbon atoms, and straight or branched chain unsaturated alkyl group having from 2 to about 3 carbon atoms, or two —$R^1$'s on the same carbon atom are ═O or ═$CR^3{}_2$. Preferably, —$R^1$ is —H, —OH, methyl, or ethyl, or two —$R^1$'s on the same carbon atom are ═O or ═$CH_2$, and further preferred is no more than about two —$R^1$ groups being other than —H. Most preferred is all —$R^1$ groups being —H.

Each —$R^3$ is independently selected from the group consisting of —H, methyl and ethyl. Preferably all —$R^3$ groups are —H.

Each —$R^4$ is independently selected from the group consisting of —$CH_3$ and —$CH_2CH_3$, or the —$R^4$'s may be joined to form a cyclic acetal such that both —$R^4$'s together are one group selected from —$(CH_2)_2$— and —$(CH_2)_3$—. Preferred is both —$R^4$ groups being methyl, or both —$R^4$ groups together being —$CH_2CH_2$—. Most preferred is both —$R^4$ groups being methyl.

Each —Z— is independently selected from the group consisting of —O—, —S—, and —$NR^3$—. Preferred is —Z— being —O— or —S—, and most preferred is both —Z— groups being the same atom selected from —O— or —S—, especially —O—.

Specifically preferred acetal groups (i.e., —$CH(ZR^4)_2$ groups) are

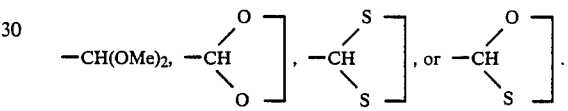

Most preferred specific acetals are

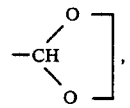

and, especially, —$CH(OMe)_2$.

Preferred —Y groups are those having terminal —C≡CH or acetal functionalities (—Y groups numbered 1 to 4 hereinabove). Most preferred —Y groups are —$(CR^1{}_2)_n$—C≡CH, wherein n is an integer of from 0 to about 5; more preferred is wherein n is an integer of from 1 to about 4; most preferred is n=3.

The processes of the present invention are useful for preparing aromatic compounds with an aliphatic ketone substituent having a labile moiety in the aliphatic portion of the substituent, comprising the following reaction step:

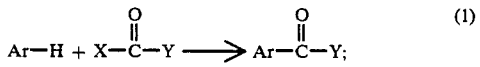

the labile portion of the —Y group may comprise unsaturated bonds (e.g., triple bond, double bond), a carbonyl or an ester in any position. Preferably the labile portion of the —Y group is a terminally unsaturated moiety, especially the terminally unsaturated groups provided in detail hereinbefore.

In the processes of the present invention, Reaction (1) hereinabove is carried out in a solvent medium at a temperature of from about −40° C. to about −100° C. using stannic chloride ($SnCl_4$) as a catalyst. Reaction (1)

hereinabove is preferably carried out at a temperature of from about −50° C. to about −80° C., more preferably of from about −60° C. to about −80° C. The time of Reaction (1) is preferably less than about 1 hour, more preferably about 30 minutes.

Preferred solvents for carrying out Reaction (1) include di-and trichlorinated hydrocarbon solvents and mixtures of such solvents with other common organic solvents (e.g., toluene, hexane, etc.), and ether solvents. More preferred solvent systems for carrying out Reaction (1) are di- and trichlorinated $C_1$-$C_2$ hydrocarbon solvents; more preferred still are dichloromethane (methylene chloride), trichloromethane (chloroform), dichloroethane, and trichloroethane; the most preferred solvent is dichloromethane.

The following Examples further describe and demonstrate the preferred embodiments within the scope of the present invention. The Examples are given solely for the purpose of illustration, and are not to be construed as limitations of the present invention, since many variations thereof are possible without departing from its spirit and scope. All temperature readings are in °C.

EXAMPLE 1

Synthesis of 2-methyl-4-(5'-hexynoyl)-6-t-butylphenol

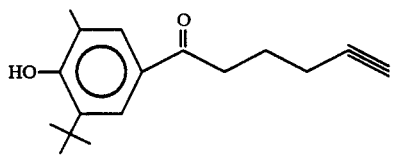

To a solution of 2-tert-butylphenol (18 ml, 117 mmol) in 117 mL methylene chloride, stirred at 0° C., is added bromine (2.1 equiv, 39 g). The reaction is allowed to reach room temperature and is stirred 15 minutes more. The product is then extracted from water using 3 100 mL portions of ether. The ether layers are combined and washed sequentially with sodium bicarbonate, and water. The resulting organic layer is dried (MgSO$_4$), filtered, and concentrated in vacuo to give the crude dibromide (2,4-dibromo-6-tert-butylphenol), which is used in the next reaction without further purification.

A flask with mechanical stirring and a reflux condenser is charged with a mixture of 10% NaOH (117 mL) and zinc (60 g). The crude dibromide from above is added as a solid in small portions. The mixture is heated to 100° C. for 30 min. After cooling to room temperature, the reacted material is filtered, and acidified in an ice bath using 6N HCl. The product is extracted with 3 100 mL portions of ether. The ether extract is washed with water (2×300 mL), dried (MgSO$_4$), filtered, and concentrated in vacuo. The crude product is dissolved in hexane (100 mL) and slurried with 50 g silica gel. The hexane is filtered off, and the silica gel is washed with 100 mL more hexane. The silica gel treatment is then repeated. The combined hexane portions are concentrated in vacuo to give mono-bromide, which is used without further purification in the next step.

To 100 mL tetrahydrofuran (THF), cooled to −78° C. under argon, is added tert-butyllithium (35.4 mL of 1.8M solution), with stirring. A sample of the mono-bromide from above (4.56 g, 20 mmol), dissolved in 5 mL THF, is added dropwise with stirring. After stirring 30 minutes at −78° C., the reaction is warmed to 0° C. and stirred 30 minutes. After re-cooling to −78° C., iodomethane (2.96 mL, 48 mmol) is added dropwise with stirring. The reaction is allowed to warm to 0° C., and stirring is continued for 30 minutes. The reaction is added to 1N HCl (ca 100 mL) and extracted with 3 100 mL portions of ether. The ether portions are combined, dried (MgSO$_4$), filtered, and chromatographed on silica gel (sg) (2% EtOAc in hexane) to give 1.04 g pure 2-tert-butyl-6-methylphenol.

To a solution of 2-tert-butyl-6-methylphenol (1.2 g, 7.3 mmol) in methylene chloride (28 ml, 1.1 equiv.), stirred under argon at −78° C., is added 5-hexynoyl chloride (1.0 g) followed by stannic chloride (0.93 mL, 1.1 equiv.). After stirring 30 minutes at −78° C., the reaction is warmed to −50° C. and stirred 5 minutes more. The mixture is then quenched with 1N HCl/ether. The product is extracted from 1N HCl with 3 portions of ether, and the ether layers are combined and washed with water. The resulting ether layer is dried (MgSO$_4$), filtered, and concentrated in vacuo to give 2.14 g crude product. The product is flash chromatographed on silica gel using 10% EtOAc in hexane to give 0.97 g 2-methyl-4-(5'-hexynoyl)-6-t-butylphenol. Crystallization from hexane gives crystals, mp 63°-64° C.

IR (CCl$_4$): 3610(s), 3430(m), 3320(s), 2960(s), 2120(w), 1675(s), 1580(s), 1340(m), 1180(s), 630(m), cm$^{-1}$.

$^1$H-NMR (CDCl$_3$) δ(ppm): 1.45(s, 9H), 1.98(q, 4H), 2.35(s, 3H), 3.10(t, 2H), 5.60(s, 1H), 7.70 (s, 1H), 7.80(s, 1H); $^{13}$C-NMR (CDCl$_3$) δ: 16.24, 18.00, 23.39, 29.58, 34.73, 36.65, 69.15, 83.86, 123.53, 125.91, 128.80, 129.51, 136.09, 158.04, 199.26 ppm.

EXAMPLE 2

Synthesis of 2-(2-Hydroxy-1,1-dimethyl-ethyl)-4-(5'-hexynoyl)-6-t-butylphenol

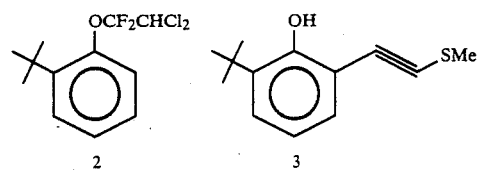

2      3

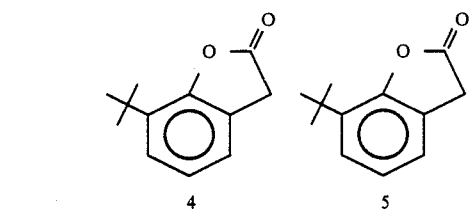

4      5

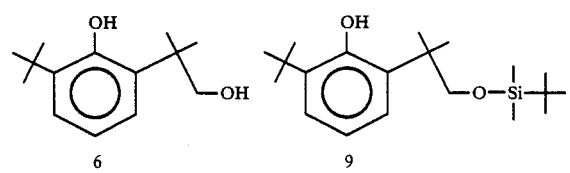

6      9

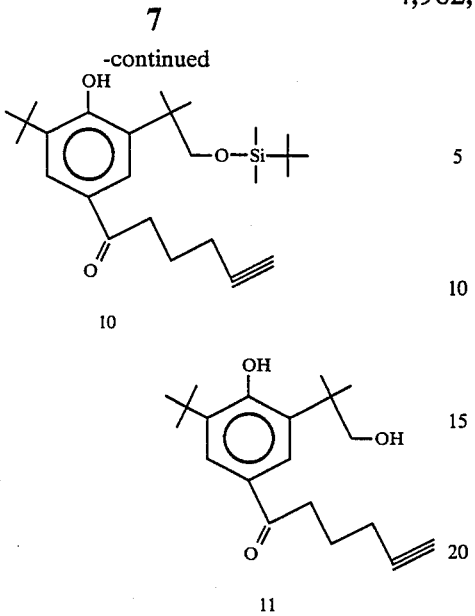

10

11

To a mixture of 47.5 g (316 mmol) of o-(t-butyl)-phenol, 91 mL of 40% KOH, and 13 mL of 40% tetra-n-butylammonium hydroxide is added at 0° a solution of ca. 100 mL of 1,1-dichloro-2,2-difluoro-ethylene in 250 mL of CH$_2$Cl$_2$. The flask is well-stoppered at 0° and the mixture is allowed to warm to room temperature and is stirred vigorously for 48 h. The reaction mixture is poured into water and extracted with pet. ether. The combined organic phase is washed with sat. NaCl and dried (MgSO$_4$). Concentration and short-path distillation gives 83.4 g of 2: bp 95°/1 torr; IR (film): 2970 (m), 1445 (m), 1310 (s), 1265 (s), 1235 (s), 1175 (s), 1165 (s), 835 (s), 755 (s) cm$^{-1}$; $^1$H-NMR (CDCl$_3$, TMS) δ: 1.40 (s, 9H), 5.95 (t, J=7 Hz, 1H), 7.0–7.5 (m, 4H).

A solution of 82.2 g (291 mmol) of 2 in 875 mL of tetrahydrofuran (THF) is treated at −78° C. with 640 mL (1.75 mol) of 2.74M nBuLi, keeping the temperature below −60° C. The mixture is stirred at −78° C. for 6 hours and then is allowed to warm very slowly to room temperature where it is stirred overnight. The reaction is cooled back to −78° C. and to it is added 41.1 g (436 mmol) of methyl disulfide. The solution is allowed to warm to 25° C., stirred for 2 hours, and is then poured into 0.1N HCl. The aqueous portion is extracted with ether and the combined organic phase is washed with sat. NaHCO$_3$ and sat. NaCl, and then dried (MgSO$_4$). GC examination of the reaction mixture reveals a very clean reaction, showing very little else besides 3. The volatile solvents are removed in the hood by distillation, with the pot temperature reaching ca. 110° C. GC analysis at this point shows an ca. 3:1 mixture of 3 and the corresponding thioester derived from hydration of the triple bond. Kugelrohr distillation (oven temp.=110°–140° C., 0.5 torr) affords 43.5 g of an approx. 3:1 mixture of 3 and the respective thioester: (Spectra of pure 3) IR (neat): 3480 (m), 2960 (m), 1430 (s), 1225 (m), 745 (s) cm$^{-1}$; $^1$H-NMR (CDCl$_3$, TMS) δ: 1.45 (s, 9H), 2.50 (s, 3H), 6.25 (s, 1H), 6.80 (m, 1H), 7.25 (m, 2H).

A mixture of 43.5 g (ca. 193 mmol) of 3 (containing 25% thioester) and 600 mL each of methanol and 3N H$_2$SO$_4$ is refluxed overnight. The reaction solution is concentrated to ca. one-half of its original volume by distilling away the volatiles, and then is cooled to 25° C. and concentrated by means of a water aspirator in the hood (this procedure removes all volatile sulfur-containing by-products). The concentrated reaction is poured into water and extracted with ether. The combined organic phase is washed with sat. NaHCO$_3$ and sat. NaCl, and then dried (MgSO$_4$). The volatiles are removed under reduced pressure and the crude lactone is recrystallized from hexane to afford 23.2 g of pure 4. The mother liquor is flash chromatographed (10% EtOAc/hex) to afford an additional 2.01 g of 4. Total yield of 4 is 25.2 g: mp 99.5°–100°; IR (CDCl$_3$): 2965 (s), 1795 (vs), 1430 (s), 1085 (s), 1070 (s) cm$^{-1}$; $^1$H-NMR (CDCl$_3$, TMS) δ: 1.40 (s, 9H), 3.65 (s, 2H), 7.15 (m, 3H); $^{13}$C-NMR (CDCl$_3$, TMS) δ: 29.50, 32.56, 34.19, 122.15, 123.54, 123.90, 125.81, 134.16, 152.65, 174.03.

To a solution of 3.80 g (20.0 mmol) of 4 and 5.0 mL (80 mmol) of iodomethane in 100 mL of THF is added portionwise at 0° C. 5.6 g (50 mmol) of potassium t-butoxide. The mixture is stirred at 0° C. for 30 min and then is warmed to 25° C. and stirred for an additional 2 hours. The reaction is poured into 0.1N HCl and the aqueous layer is extracted with ether. The combined organic phase is washed with sat. NaHCO$_3$ and sat. NaCl, and then dried (MgSO$_4$). The crude, concentration reaction mixture is recrystallized from hexane to afford 2.21 g of pure 5. The mother liquor is Kugelrohr distilled (oven temp=160° C., 0.5 torr) to provide an additional 1.19 g of 5. The total yield of 5 is 3.40 g: mp 84°–85°; IR (CDCl$_3$): 2970 (s), 1795 (vs), 1430 (s), 1280 (s), 1055 (s) cm$^{-1}$; $^1$H-NMR (CDCl$_3$, TMS) δ: 1.40 (s, 9H), 1.50 (s, 6H), 7.15 (m, 3H); $^{13}$C-NMR (CDCl$_3$ TMS) δ: (off-resonance multiplicity) 25.38 (q), 29.58 (q), 34.21 (s), 42.09 (s), 120.32 (d), 124.14 (d), 125.59 (d), 134.13 (s, two carbons), 150.11 (s), 180.82 (s).

A solution of 1.14 g (30.0 mmol) of lithium aluminum hydride in 50 mL of ether is treated at 0° C. with 5.45 g (25.0 mmol) of 5. The reaction mixture is warmed to 25° C. and stirred for 1 hour. The excess hydride is decomposed at 0° C. with 25 mL of ethyl acetate followed by 100 mL of a 1:1 mixture of sat. NH$_4$Cl and water. The reaction is filtered through a short pad of celite, washing it well with ether. The combined organic layer is washed with sat. NaCl and dried (MgSO$_4$). Concentration leaves essentially pure 6: mp 67°–68° C.; IR (CCl$_4$): 3640 (m), 3290 (s, br), 2960 (s), 1425 (m), 1385 (m), 1245 (m), 1030 (m) cm$^{-1}$; $^1$H-NMR (CDCl$_3$, TMS) δ: 1.40 (s, 15H), 1.85 (br s, alcoholic OH, 1H), 3.65 (br s, 2H), 6.6–7.3 (m, 3H), 9.05 (s, phenolic OH, 1H); $^{13}$C-NMR (CDCl$_3$, TMS) δ(off-resonance multiplicity): 25.45 (q), 29.99 (q), 34.97 (s), 39.75 (s), 74.13 (t), 118.96 (d), 125.25 (d), 125.58 (d), 133.33 (s), 138.25 (s), 155.28 (s).

To a mixture of 2.81 g (12.7 mmol) of 6, 2.37 g (15.8 mmol) of tert-butyldimethylchlorosilane, and 0.38 g (3.2 mmol) of 4-dimethylaminopyridine in 60 mL of methylene chloride is added, at room temperature, 5.23 mL (38.0 mmol) of triethylamine. The reaction mixture is stirred overnight at 25° C. and is then poured into water. The aqueous layer is extracted with ether and the combined organic layer is washed with sat. NaCl and dried (MgSO$_4$). The crude, concentrated reaction solution is flushed through a short column of silica gel eluting with 2% EtOAc/hex (R$_f$ of 9=0.72) directly into a round-bottomed flask. Concentration affords 4.06 g of 9: IR (film): 3225 (s, br), 2950 (s), 2930 (s), 1385 (s), 1250 (s), 1050 (s), 835 (s), 780 (s) cm$^{-1}$; $^1$H-NMR (CDCl$_3$, TMS) δ: 0.15 (s, 6H), 0.95 (s, 9H), 1.45 (s, 15H), 3.70 (s, 2H), 6.6–7.3 (m, 3H), 9.50 (s, 1H).

A solution of 4.38 g (13.0 mmol) of 9 in 70 mL of methylene chloride is sequentially treated at −78° C. with 1.85 g (14.3 mmol) of 5-hexynoyl chloride and 1.68 mL (14.3 mmol) of stannic chloride. The mixture is stirred at −78° C. for one hour and is then allowed to warm up to ca. −50° C. and stirred there for 5 min. The reaction is poured into 0.1N HCl and the layers are separated. The aqueous portion is extracted with ether and the combined organic phase is washed with sat. NaHCO$_3$ and sat. NaCl, and then dried (MgSO$_4$). TLC (10% EtOAc/hexane) showed only a trace of 9 (R$_f$=0.70) along with the nearly pure 10 (R$_f$=0.38). The crude, concentrated 10 is diluted with 75 mL of THF and to it is added at 25° C., 8.19 g (26.0 mmol) of tetra-n-butylammonium fluoride trihydrate. After stirring the mixture for one hour at 25° C. it is poured into water and the aqueous layer is extracted with ether. The combined organic phase is washed with sat. NaCl and dried (MgSO$_4$). TLC (20% EtOAc/hexane) shows predominantly 11 (R$_f$=0.22), with no 10 (R$_f$=0.60) remaining. Flash chromatography affords 3.21 g of 11: mp 91°-93°; IR (CHCl$_3$): 3620 (m), 3310 (s), 3200 (m, br), 2970 (s), 2110 (w), 1655 (s), 1585 (s), 1270 (s), 635 (m) cm$^{-1}$; $^1$H-NMR (CDCl$_3$, TMS) δ: 1.40 (s, 15H), 1.7-2.3 (m, 5H), 3.05 (t, 2H), 3.80 (d, 2H), 5.40 (t, 1H), alcoholic OH), 7.80 (s, 2H), 10.95 (s, 1H, phenolic OH); $^{13}$C-NMR (CDCl$_3$, TMS) δ(off-resonance multiplicity): 18.03 (t), 23.71 (t), 25.38 (q), 29.68 (q), 35.25 (s), 36.58 (t), 40.06 (s), 69.22 (d), 73.55 (t), 83.73 (s), 126.40 (d), 126.69 (d), 127.06 (s), 133.92 (s), 138.34 (s), 161.54 (s), 200.91 (s).

EXAMPLE 3

Synthesis of 2-Allyl-4-(5′-hexynoyl)-6-t-butylphenol

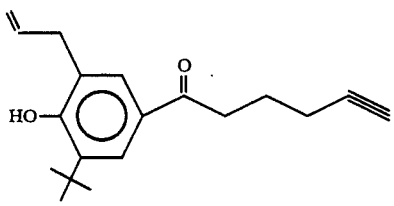

To a stirred solution of o-(t-butyl)-phenol (11.3 g; 75 mmol) in acetone (150 ml) is added allyl bromide (10.9 g, 1.2 equiv.) and anhydrous K$_2$CO$_3$. After stirring 18 hr at reflux, the reaction is added to water (200 ml) and extracted with 3×150 ml portions of petroleum ether. The combined organic layers are dried (MgSO$_4$), filtered, and concentrated in vacuo to give the crude product, which is purified by silica gel (sg) chromatography (hexane elution) to yield 1-prop-2-enyloxy-2-t-butylbenzene (11.6 g; 81% yield).

A glass lined 3 L vessel is charged with 1-prop-2-enyloxy-2-t-butylbenzene (11.6 g; 61 mmol), Ac$_2$O (160 ml), and NaOAc (10 g). After heating at 200° C. for 18 hr, the mixture is poured into 200 g ice, with stirring for 15 min. It is then extracted with 3×300 ml portions of ether. The combined ether layers are slowly added to an ice-cooled flask containing NaHCO$_3$ and stirred for 40 min. The ether layer is then separated, washed with 2×300 ml saturated NaCl solution, dried (MgSO$_4$), filtered, and concentrated in vacuo to give 17.2 g crude product. Chromatography using 3:1 petroleum ether/CH$_2$Cl$_2$ then gives 7.69 g pure 1-acetoxy-2-allyl-6-t-butylbenzene (54% yield).

To a solution of 1-acetoxy-2-allyl-6-t-butylbenzene (7.69 g) in dry ether (66 ml) is added lithium aluminum hydride (LAH) (2.2 g) with stirring. After 30 minutes at reflux, the reaction is acidified using 3N HCl (ca. 75 ml) with ice bath cooling. The mixture is then poured into water (200 ml) and extracted with 3×100 ml ether. The ether layers are combined, dried (MgSO$_4$), filtered, and concentrated in vacuo to give 5.4 g product, which is purified by silica gel chromatography (50:1 ether/CH$_2$Cl$_2$) to give pure 2-allyl-6-t-butylphenol (4.69 g; 76% yield).

A solution of 2-allyl-6-t-butylphenol (0.57 g; 3 mmol) in dry CH$_2$Cl$_2$ (12 ml) is cooled to −78° C., and 5-hexynoyl chloride (0.43 g; 3.3 mmol) is added via syringe, followed by SnCl$_4$ (0.375 ml) added dropwise via syringe, with stirring under Argon. After 30 min the reaction is allowed to warm to 0° C. and is stirred at that temperature for 5 min; it is then quenched with ca 1 ml of 3N HCl. The reaction is poured into 100 ml water and extracted with 3×50 ml portions of ether. The combined ether layers are washed with 150 ml portions of water until the aqueous layer is neutral (pH test). The ether layer is dried (MgSO$_4$), filtered, and concentrated in vacuo to give crude product, which is chromatographed with 20:1 hexane/EtOAc, giving 0.64 g 2-allyl-4-(5-hexynoyl)-6-t-butylphenol (77% yield). The product is recrystallized from hexane at 0° C. to give crystals melting at 62°-63° C.

$^{13}$C-NMR (CDCl$_3$) δppm: 18.0, 23.3, 29.6, 34.7, 35.9, 36.6, 69.0, 83.9, 117.9, 124.8, 126.5, 129.0, 129.4, 135.6, 136.9, 158.2, 198.9.

IR (CCl$_4$): 3500 cm$^{-1}$ (m), 3300 (m), 2950 (s), 2100 (w), 1665 (s), 1580 (m), 1410 (m), 1360 (m), 1310 (m), 1250 (m), 1180 (s), 1140 (m), 920 (m).

$^1$H-NMR (CDCl$_3$) (60 mH$_2$) δppm: 1.45 (s, 9H), 1.8-2.4 (m, 5H), 3.15 (t, 2H), 3.60 (d, 2H), 5.1-5.4 (m, 1H), 6.08 (s, 1H), 7.80 (d, 1H), 8.0 (d, 1H).

GC/EI: C$_{19}$H$_{24}$O$_2$.

MS: M$^+$ at 284.

EXAMPLE 4

Synthesis of 2-Methyl-4-(5′-hexynoyl)-6-trifluoromethylphenol

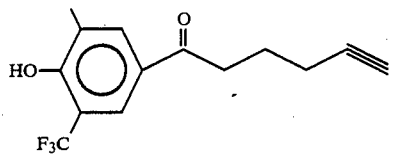

To a solution of o-trifluoromethylphenol (3.0 g; 19 mmol) in CH$_2$Cl$_2$ (20 ml) is added bromine (6.4 g; 39.9 mmol) at 25° C. with stirring, and stirring is continued for 2.5 hours. The reaction is then poured into a separatory funnel with 100 ml of water plus 100 ml ether. The aqueous portion is extracted with 3×100 ml portions of ether. The organic fractions are combined and washed with 1M sodium bicarbonate (300 ml) followed by a water (200 ml) wash. The mixture is then dried (MgSO$_4$), filtered, and concentrated in vacuo to give 5.8 g crude 2,4-dibromo-6-trifluoromethylphenol. To remove contaminating mono-brominated material, the reaction above is repeated on the crude product (6.4 g bromine) to give pure product (5.77 g of 2,4-dibromo-6-trifluoromethylphenol) used in the next step without further purification.

A solution of 2,4-dibromo-6-trifluoromethylphenol (5.77 g; 18 mmol) is dissolved in dry THF (45 ml), and s-butyllithium (21 ml of 1.7M solution) is added dropwise with stirring at −78° C. under argon. After stirring at −78° C. for 30 minutes, the mixture is allowed to warm to 0° C. and is stirred 40 minutes more. The reaction is quenched with 1N HCl and extracted from 1N HCl (50 ml) with 3×50 ml portions of ether. The combined ether portions are washed with 1M sodium bicarbonate (100 ml) then dried (MgSO4), filtered and concentrated in vacuo to give 3.84 g crude product. Chromatography on silica gel (95:5 petroleum ether/ether) thus gives 2-bromo-6-trifluoromethylphenol.

t-Butyllithium (1.7 ml of a 1.8M solution of hexane; 3 equiv.) is added to THF (1 ml) and cooled to −78° C. under argon with stirring, and a solution of 2-bromo-6-trifluoromethylphenol in dry THF (1 ml; 1 mmol) is added dropwise via syringe. The reaction is stirred 30 minutes, and then iodomethane (340 mg; 2.4 equiv.) is added dropwise via syringe at −78° C. under argon, with stirring. The mixture is allowed to warm to 0° C. with stirring over 15 minutes, and stirring is continued for 45 minutes more. The reaction is then quenched with 1N HCl (3 ml) and extracted from 1N HCl (10 ml) with 3×10 ml portions of ether. The combined ether portions are washed with water (3×20 ml portions: pH tests neutral), and the solution is then dried (MgSO4), filtered, and concentrated in vacuo to give crude 2-methyl-6-trifluoromethylphenol, which is chromatographed on silica gel with 5% ether in petroleum ether to give pure product.

The resulting 2-methyl-6-trifluoromethylphenol is converted to 2-methyl-4-(5'-hexynoyl)-6-trifluoromethylphenol by reaction with 5-hexynoyl chloride using a modified Friedel-Crafts reaction as described in Example 3 above.

EXAMPLE 5

Synthesis of 1-Methoxy-4-(5'-hexynoyl)-benzene

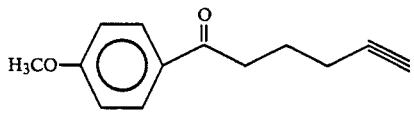

To a solution of anisole (10.8 g, 100 mmol) in methylene chloride (100 ml) stirred at −60° C. is added 5-hexynoyl chloride (13.0 g, 1.00 eq) followed by stannic chloride (26.4 g, 1.01 eq) over a 10 minute period. The reaction mixture is warmed to −50° C. and is stirred for 5 minutes. The mixture is quenched with 3N HCl and the layers are separated. The methylene chloride layer is extracted twice with 3N HCl, then twice with water, then concentrated in vacuo. Yield of crude product is 18.9 g (94% yield). This is recrystallized from hexane to afford 6.7 g of 1-methoxy-4-(5'-hexynoyl)benzene. Preparative HPLC of the mother liquor affords an additional 3.5 g of this product; m.p. 49.5°–51° C.

IR (Nujol mull) 3280, 1680, 1600, 1511, 1340, 1308, 1257, 1207, 1168, 1021, 980, 817, 702, 662, cm$^{-1}$.

$^1$H-NMR (CDCl$_3$) 1.95 (m, 2H), 2.08 (t, 1H), 2.36 (m, 2H), 3.08 (t, 2H), 3.84 (s, 3H), 6.96 (d, 2H), 7.98 (d, 2H), ppm;

$^{13}$C-NMR (CDCl$_3$) 17.6, 22.8, 36.2, 55.0, 68.8, 83.5, 113.4, 129.9, 163.1, 197.5, ppm.

EXAMPLE 6

Synthesis of 4-(5'-Hexynoyl)toluene

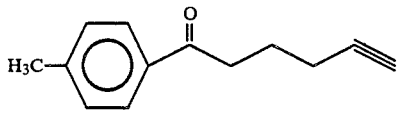

A solution of 5-hexynoyl chloride (12.19 g, 1.68 mmol) and toluene (2.0 ml, 1.12 eq) in methylene chloride (30 ml) is cooled to −60° C. Stannic chloride (4.80 g, 1.11 eq) is added to the solution in two portions five minutes apart and the mixture is allowed to warm to −40° C. over a 15 minute period. The reaction mixture is quenched with 2N HCl and the layers are separated. The methylene chloride layer is extracted twice with 2N HCl, then extracted twice with water, and concentrated in vacuo. The yield of the crude 4-(5'-hexynoyl)-toluene is 2.15 g.

EXAMPLE 7

Synthesis of 1,2-Diethoxy-4-(5'-hexynoyl)benzene

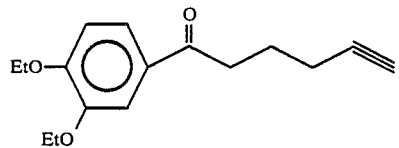

A solution of 1,2-diethoxybenzene (1.66 g, 10.0 mmol) and 5-hexynoyl chloride (1.31 g, 1.00 eq) in methylene chloride (20 ml) is cooled to −60° C. Stannic chloride (2.66 g, 1.02 eq) is slowly added to the solution and the mixture is stirred at −60° C. for 10 minutes. The reaction mixture is quenched with 3N HCl and the layers are separated. The methylene chloride layer is extracted with 3N HCl, then extracted twice with water, and concentrated in vacuo. The yield of the crude 1,2-diethoxy-4-(5'-hexynoyl)benzene is 2.67 g.

EXAMPLE 8

Synthesis of 5'-Hexynoylbenzene

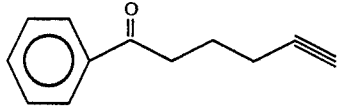

A solution of benzene (3.78 g, 48.5 mmol) and 5-hexynoyl chloride (6.58 g, 1.04 eq) in methylene chloride (100 ml) is cooled to −60° C. Stannic chloride (13.4 g, 1.05 eq) is added dropwise to the solution over a minute period. The resulting mixture is warmed to −45° C., and after 10 minutes the reaction mixture is quenched with 2N HCl and the layers are separated. The methylene chloride layer is extracted twice with 2N HCl, then extracted twice with water, and concentrated in vacuo. The yield of the crude 5'-hexynoylbenzene is 4.31 g.

EXAMPLE 9

Synthesis of 4-(5'-Hexynoyl)-2,6-di-tert-butylphenol)

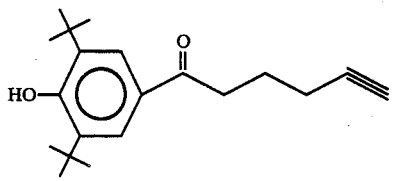

A solution of 2,6-di-tert-butylphenol (206.3 g, 1.00 mmol) in methylene chloride (2L) is cooled to −40° C. The 5-hexynoyl chloride (131.1 g, 1.01 eq) is added in one portion and the resultant solution is cooled to −53° C. and the stannic chloride (120 ml, 1.02 eq) is added dropwise to the solution over a half hour period. The temperature of the reaction mixture is dropped to −60° C. over the addition period. After stirring for an additional 5 minutes, the reaction mixture is quenched with 3N HCl, then extracted twice with water, and concentrated in vacuo. The yield of the crude 4-(5'-hexynoyl)-2,6-di-tert-butylphenol is 322.1 g. The crude product is recrystallized from hexane at −30° C. to yield 259 g (86% yield) of 4-(5'-hexynoyl)-2,6-di-tert-butylphenol, mp 68°–68.5° C.

IR: 3590, 3320, 3270, 1658, 1587, 1419, 1375, 1362, 1312, 1257, 1223, 189, 1103, 1004, 875, 663, 616 cm$^{-1}$.

$^1$H NMR (CDCl$_3$): 1.56 (s, 18H), 2.08 (m, 3H), 2.41 (m, 2H), 3.29 (t, 2H), 5.96 (s, 1H), 7.97 (s, 2H) ppm.

$^{13}$C NMR (CDCl$_3$): 17.8, 23.2, 29.9, 34.1, 36.2, 68.8, 83.6, 125.5, 128.7, 135.7, 158.1, 198.6 ppm.

EXAMPLE 10

The compound

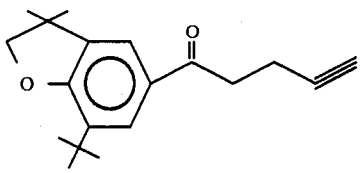

is prepared from compound 6 of Example 2. To a solution of 1.78 g (8.00 mmol) of 6 in 30 mL of dichloromethane is added sequentially at 0° C., 0.68 mL (8.8 mmol) of methanesulfonyl chloride (MsCl) and 2.80 mL (20.0 mmol) of triethylamine (Et$_3$N). The reaction is stirred for one hour at 0° C. and is poured into saturated NaCl. The aqueous layer is extracted with ether and the combined organic phase is washed with saturated NaCl and dried (MgSO$_4$). Kugelrohr distillation (oven temp = 110° C., 0.5 torr) provides 1.49 g (91%) of

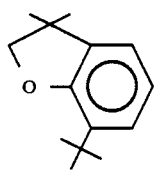

IR (neat): 2960 (s), 2870 (m), 1425 (m), 995 (m), 745 (m) cm$^{-1}$; $^1$H-NMR (CDCl$_3$, TMS) δ: 1.25 (s, 6H), 1.35 (s, 9H), 4.15 (s, 2H), 6.7–7.2 (m, 3H); $^{13}$C-NMR (CDCl$_3$, TMS) δ (off-resonance multiplicity): 27.42 (q), 29.36 (q), 34.07 (s), 41.39 (s), 83.57 (t), 119.84 (d), 120.31 (d), 124.58 (d), 133.08 (s), 136.85 (s), 157.11 (s).

A solution of 1.65 g (8.10 mmol) of 7 in 40 mL of dichloromethane is sequentially treated at −78° C. with 8.90 mmol of 4-pentynoyl chloride and 1.05 mL (8.90 mmol) of stannic chloride. The mixture is stirred at −78° C. for 1 hour and is then warmed up to ca. −50° C. and is stirred there for 5 minutes. The reaction is then poured into 0.1N HCl and the layers are separated. The aqueous portion is extracted with ether and the combined organic phase is washed with saturated NaHCO$_3$ and saturated NaCl, and then dried (MgSO$_4$). Flash chromatography (5% EtOAC/hex) provides a 90% yield of 8.

While particular embodiments of the present invention have been described, it will be obvious to those skilled in the art that various changes and modifications to the compounds and compositions disclosed herein can be made without departing from the spirit and scope of the invention. It is intended to cover, in the appended claims, all such modifications that are within the scope of this invention.

MBG:dr
(AP2:N-502)

What is claimed is:

1. A process for the preparation of a compound having the chemical structure:

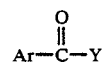

wherein Ar has the structure:

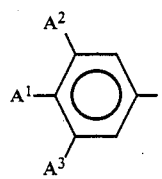

wherein —A$^1$ is selected from the group consisting of —OH and —O$_2$CR, wherein —R is a straight or branched chain alkyl group having from 1 to about 10 carbon atoms; —A$^2$ is selected from the group consisting of unsubstituted or substituted, saturated or unsaturated, straight, branched or cyclic alkyl having from 1 to about 10 carbon atoms, and trimethylsilyl, and wherein substituents of —A$^2$ are nil or one or more of the group consisting of halo, —OR$^3$, —O$_2$CR$^3$, —CO$_2$R$^3$, and —C(O)R$^3$; wherein —A$^3$ is selected from the group consisting of t-butyl, trimethylsilyl, and trifluoromethyl; and wherein —Y is a terminally unsaturated group selected from the group consisting of:

1. —(CR$^1{}_2$)$_n$—C≡CH, wherein n is an integer from 0 to about 5;
2. —(CR$^1{}_2$)$_n$—CR$^3$=CH$_2$, wherein n is an integer from 0 to about 5;
3. —(CR$^1{}_2$)$_n$—CR$^3$=C=CH$_2$, wherein n is an integer from 0 to about 5; and
4. —(CR$^1{}_2$)$_n$—CH(ZR$^4$)$_2$, wherein n is an integer from 1 to about 5;

and wherein each —R$^1$ is independently selected from the group consisting of —H, —OR$^3$, —NR$^3{}_2$, —NR$^3{}_3{}^+$, —N(R$^3$)C(O)R$^3$, —O$_2$CR$^3$, —CO$_2$R$^3$ —C(O)NR$^3{}_2$, straight or branched chain saturated alkyl group having from 1 to about 3 carbon atoms, and straight or branched chain unsaturated alkyl group having from 2 to about 3 carbon atoms, or two —$R^1$'s on the same carbon atom are =O or =$CR^3_2$; each —$R^3$ is independently selected from the group consisting of —H, methyl and ethyl; each —$R^4$ is independently selected from the group consisting of —$CH_3$ and —$CH_2CH_3$, or the —$R^4$'s may be joined to form a cyclic acetal such that both —$R^4$'s together are one group selected from —$(CH_2)_2$— and —$(CH_2)_3$—; and each —Z— is independently selected from the group consisting of —O—, —S—, and —$NR^3$—;

comprising the step of reacting the compounds Ar—H and

wherein —X is —Cl or —Br, and wherein said reaction step is carried out in a solvent selected from dichlorinated and trichlorinated $C_1$-$C_2$ hydrocarbon solvents, at a temperature of from about −40° C. to about −100° C. using stannic chloride as a catalyst.

2. The process of claim 1 wherein —$A^1$ is —OH.

3. The process of claim 2 wherein —$A^2$ and —$A^3$ are the same substituent.

4. The process of claim 2 wherein —$A^2$ is unsubstituted or substituted with hydroxy or halo and —$A^3$ is t-butyl.

5. The process of claim 4 wherein —$A^2$ is unsubstituted.

6. The process of claim 5 wherein —$A^2$ and —$A^3$ are both t-butyl.

7. The process of claim 1 wherein —Y is selected from the group consisting of —$(CR^1_2)_n$—C≡CH, —$(CR^1_2)_n$—$CR^3$=$CH_2$, and —$(CR^1_2)_n$—$CR^3$=C=$CH_2$.

8. The process of claim 6 wherein —Y is selected from the group consisting of —$(CR^1_2)_n$—C≡CH, —$(CR^1_2)_n$—$CR^3$=$CH_2$, and —$(CR^1_2)_n$—$CR^3$=C=$CH_2$.

9. The process of claim 8 wherein all —$R^1$ and —$R^3$ are H.

10. The process of claim 8 wherein —Y is selected from —$(CR^1_2)_n$—C≡CH.

11. The process of claim 10 wherein all —$R^1$ are —H.

12. The process of claim 11 wherein n=3.

13. The process of claim 6 wherein said reaction is carried out in said solvent medium at a temperature of from about −50° C. to about −80° C.

14. The process of claim 9 wherein said reaction is carried out in said solvent medium at a temperature of from about −50° C. to about −80° C.

15. The process of claim 12 wherein said reaction is carried out in said solvent medium at a temperature of from about −50° C. to about −80° C.

16. The process of any of claims 1, 6, 9, 12 and 15 wherein said solvent is dichloromethane.

* * * * *

UNITED STATES PATENT AND TRADEMARK OFFICE
CERTIFICATE OF CORRECTION

PATENT NO. : 4,982,006
DATED : January 1, 1991
INVENTOR(S) : Thomas T. Hudec

It is certified that error appears in the above-identified patent and that said Letters Patent is hereby corrected as shown below:

In column 6, lines 52-60, " 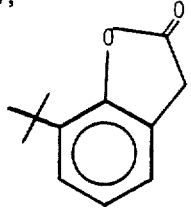 "

should be

-- 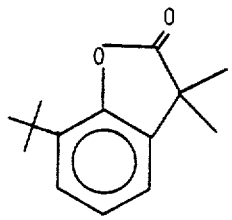 --.

Signed and Sealed this

Nineteenth Day of May, 1992

Attest:

DOUGLAS B. COMER

Attesting Officer     Acting Commissioner of Patents and Trademarks